United States Patent [19]

Campbell et al.

[11] Patent Number: 4,946,958

[45] Date of Patent: Aug. 7, 1990

[54] CHEMILUMINESCENT ACRIDINIUM LABELLING COMPOUNDS

[75] Inventors: Anthony K. Campbell, Cardiff; James S. Woodhead, Machen; Ian Weeks, Cardiff, all of United Kingdom

[73] Assignee: The Welsh National School of Medicine, Cardiff, United Kingdom

[21] Appl. No.: 251,954

[22] Filed: Sep. 26, 1988

Related U.S. Application Data

[63] Continuation of Ser. No. 865,957, May 19, 1986, abandoned, which is a continuation of Ser. No. 448,191, Dec. 9, 1982, abandoned.

[30] Foreign Application Priority Data

Dec. 11, 1981 [GB] United Kingdom ............... 8137522

[51] Int. Cl.$^5$ ................... C07D 219/04; C07K 15/28
[52] U.S. Cl. ................................. 546/104; 546/102; 546/107; 530/387; 530/802; 530/388; 530/389; 436/501; 436/503; 436/548
[58] Field of Search ....................... 546/102, 104, 107

[56] References Cited

U.S. PATENT DOCUMENTS

| | | | |
|---|---|---|---|
| 3,352,791 | 11/1967 | Sheehan et al. | 546/102 X |
| 3,431,264 | 3/1969 | Sheehan et al. | 546/102 X |
| 3,689,391 | 9/1972 | Ullman | 546/102 X |
| 3,817,837 | 6/1974 | Rubenstein et al. | |
| 4,199,559 | 4/1980 | Ullman et al. | |
| 4,277,437 | 7/1981 | Maggio | 422/61 |
| 4,376,110 | 3/1983 | David et al. | 436/513 |
| 4,478,817 | 10/1984 | Campbell et al. | 436/547 X |
| 4,745,181 | 5/1988 | Law et al. | 530/387 |
| 4,767,718 | 8/1988 | Meyers | 436/501 |

FOREIGN PATENT DOCUMENTS

| | | | |
|---|---|---|---|
| 0082636 | 6/1983 | European Pat. Off. | |
| 0212951 | 3/1987 | European Pat. Off. | |
| 0216553 | 4/1987 | European Pat. Off. | 546/102 |
| 3628573 | 2/1988 | Fed. Rep. of Germany | 546/104 |
| 1316363 | 5/1973 | United Kingdom | |
| 1461877 | 1/1977 | United Kingdom | 546/102 |
| 2008247 | 5/1979 | United Kingdom | |
| 1548741 | 7/1979 | United Kingdom | |
| 2025609 | 1/1980 | United Kingdom | |
| 2044449 | 10/1980 | United Kingdom | |

OTHER PUBLICATIONS

Hersh, et al., Analytical Biochemistry, vol. 93, pp. 267-271, (1979).
Pratt, et al., Journal of Immunological Methods, vol. 21, pp. 179-184, (1978).
Schroeder, et al., Clin. Chem., 27/8, pp. 1378-1384, (1981).
Weeks, et al., Clin. Chem., 29/8, pp. 1474-1479, (1983).
Hart et al., Jounral of Immunological Methods, vol. 101, pp. 91-96, (1987).
"Chemiluminescent Labels in Immunoassay", *Bioluminescence and Chemiluminescence*, 1981, By J. Simpson et al., pp. 673-679.
"Chemiluminescene Labelled Antibodies and Their Applications in Immunoassays", *Luminescent Assays Perspectives in Endocrinology and Clinical Chemistry*, vol. 1, 1982, By J. Woodhead et al., pp. 147-155.
"The Preparation and Properties of a Chemiluminescent Derivative of 17β-Estradiol", *Luminescent Assays Perspectives in Endocrinology and Clinical Chemistry*, vol. 1, By A. Patel et al., pp. 181-189.
"The Chemistry of Bioluminescence", *Review Lecture*, 215, 1982, by F. McCapra, 247-272.
"Proceedings of the Physiological Society", *Journal of Physiology*, vol. 306, Apr. 1980, By A. Campbell et al., pp. 4-5.
Patel et al., Chemical Abstracts, vol. 97:85407p, (1982).
Collins et al., Immunoassays for Clinical Chemistry, "Chemiluminescence Immunoassays for Plasma Steroids and Urinary Steroid Metabolites", pp. 373-397, (1981).
Schroeder et al., "Immunochemiluminometric Assay for Hepatitis B Surface Antigen", Clinical Chemistry, 1981, 27: 1378-1384.
Woodhead et al., "Chemiluminescent Labelled Antibody Techniques", Monoclonal Antibodies and Developments in Immunoassay, (1981), ed. Albortini A. & Ekins, pp. 135-145.
Simpson et al., "A Stable Chemiluminescent-Labelled Antibody for Immunological Assays", Nature, 1979, 279: pp. 646-647.
Ekins et al., Pure and Applied Chemistry, vol. 57, "The Development of High Sensitivity Pulsed Light," Time-Resolved Fluoroimmunoassays, 1985, pp. 473-482.

*Primary Examiner*—Diana G. Rivers

[57] ABSTRACT

A compound for use as a chemiluminescent label in immunoassay comprises an aryl acridinium ester linked to an N-succinimidyl moiety. The compound is conveniently linked to a monoclonal antibody or other protein and is used in a two-site immunoassay for the quantitation of an antigen of interest, by initiation of the luminescent reaction and subsequent measurement of the photonic emission of the immune complex formed during the immunological reaction.

7 Claims, No Drawings

CHEMILUMINESCENT ACRIDINIUM LABELLING COMPOUNDS

This application is a continuation of application Ser. No. 06/865,957, filed May 19, 1986, which is a continuation of Ser. No. 06/448,191, filed Dec. 9, 1982, both now abandoned.

This invention relates to methods designed for use in the analysis, assay, or location of proteins, polypeptides, and other substances of biological interest by linking ("labelling") them to another molecule or molecules which can take part in a reaction resulting in the emission of light. The labelled substance, to be termed "luminescent reagent", may be used in various types of biological investigations, preferably immunoassays and protein binding assays. The amount of the "luminescent reagent" is measured by recording the light emitted after producing the appropriate conditions required for the luminescent reaction to take place. Here, the luminescent reaction is one which generates chemiluminescence which is distinguished from fluorescence or phosphorescence. The use of the "luminescent reagent" enables the analysis, assay, or location of proteins or other substances of biological interest to be carried out without experiencing any of the disadvantages associated with the use of radioactive labelled substances such as are commonly used at present. These disadvantages are as follows. Firstly, the formation of such a radioactive reagent involves the use of highly radioactive and hence potentially hazardous species. Secondly, the shelf-life of such a radioactive reagent is often short because of its continuous decay. Further, the emission of radiation from the radio-isotope may be deleterious to the substance to which the radio-isotope is linked. Thirdly, it is often difficult to label proteins sufficiently to provide a sensitively and rapidly detectable reagent.

In contrast, the "luminescent reagent" is non-radiotoxic, stable, and can be quantified both rapidly and in small amounts.

In a preferred form the invention comprises a compound consisting of aryl acridinium ester, linkage and N-succinimidyl ester moieties. This compound undergoes a light emitting reaction in the presence of a dilute aqueous solution of sodium hydroxide and hydrogen peroxide and the amount of compound can be quantified by measurement of the intensity of the emitted light or rate of photon emission. Further the compound reacts with other substances containing primary and second aliphatic amines to yield chemiluminescent derivatives. The compound has the advantage of being stable under normal storage conditions and of reacting with the aforementioned amines under mild reaction conditions.

The compound can be represented by the general formula:

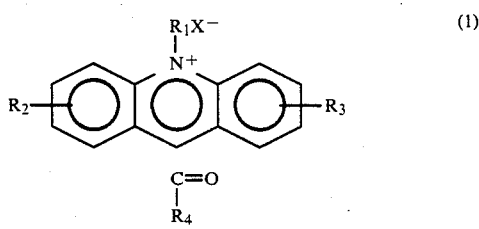

(1)

in which $X^-$ is any anion, $R_1$ represents H, $C_1$–$C_{10}$ optionally substituted alkyl, alkenyl, alkynyl or aryl, $R_2$, $R_3$ are preferably, hydrogen, amino, substituted amino, carboxyl, hydroxyl, alkoxyl, nitro-, or halide substituents, and $R_4$ is preferably an optionally substituted phenoxy-moiety. According to a preferred feature of the invention an ester linkage exists between the acridinium and phenyl moieties as exemplified in the following formula:

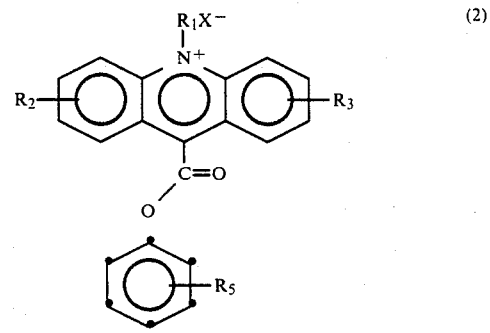

(2)

where $R_5$ comprises one of the following:

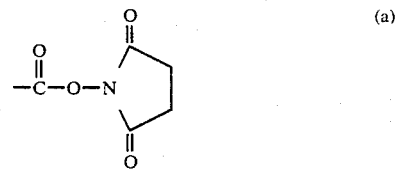 (a)

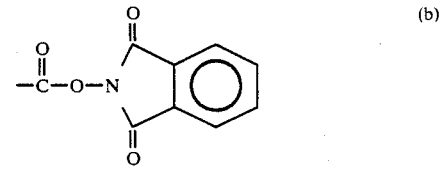 (b)

 (c)

 (d)

 (e)

 (f)

where $R_6$ represents groups such as $R_1$ and Y represents a halide. Preferably $R_5$ is linked to the phenyl residue via carbon, nitrogen or oxygen containing groups which are optionally substituted by substituents of a hydrophilic nature.

From another aspect of the invention the labelling compound is prepared by reacting an acridine with a cyanide, and thence converting the product via a carboxy derivative to a halocarbonyl acridine derivative. The acridine derivative may be further reacted with a phenolic moiety substituted with one of the groups defined above as $R_5$, and the product may be methylated at position 10. In some cases the $R_5$ moiety, or part thereof, or the linking group is protected before methylation, for example by amidation, esterification or acylation.

Thus in a particular example a N-hydroxysuccinimidyl ester is synthesised via the following route. Acridine is reacted with potassium cyanide and benzoyl chloride so as to yield a 9-cyano-derivative which is subsequently purified by recrystallisation. The material so obtained is reacted with sulphuric acid, thence sodium nitrite to yield the 9-carboxy-derivative which is purified, dried and reacted with thionyl chloride to give the 9-chlorocarbonyl-derivative. This is allowed to react with N-succinimidyl 3-(4-hydroxyphenyl) propionate to yield the corresponding ester of 9-carboxyacridine. The product is methylated at the 10-position, preferably using dimethyl sulphate or methyl fluorosulphonate to yield the final chemiluminescent product which is isolated by trituration with ether followed by filtration and dessication. An alternative method involves the formation of 9-chlorocarbonyl acridine as described above thence formation of the corresponding methyl ester using methanol followed by methylation at the 10-position preferably using dimethyl sulphate or methyl fluorosulphonate. This is then converted to the corresponding carboxylic acid by hydrolysis thence to the corresponding acyl chloride by reaction with thionyl chloride. The product of this reaction is then mixed with N-succinimidyl-3(4-hydroxyphenyl) propionate to yield the final product which is isolated by trituration.

According to a further aspect of the invention a luminescent labelling material comprises an acridinium compound as defined, linked to a protein or polypeptide or other organic substance of biological interest to provide a stable immunologically reactive luminescent reagent. The compounds represented by formulae (1) and (2) above are capable of reacting with proteins at temperatures between 0° and 40° C. under aqueous conditions optionally in the presence of organic solvents to yield "luminescent reagents" which are preferably stable and immunologically active. The reaction which results in the formation of the "luminescent reagent" is complete preferaby within 30 minutes, more preferably within 5 minutes, such that at least one mole, and preferably at least three or ten moles of chemiluminescent compound are incorporated into each 1 mole of protein, excess chemiluminescent label is inactivated with lysine which also acts to dissociate non-covalent interactions between chemiluminescent compound and protein.

Preferably the labelled reagents are antibodies more preferably monoclonal antibodies which, when labelled, can be purified so as to be free of excess chemiluminescent compound by gel permeation chromatography preferably in a buffer system containing non-immune gamma globulins.

From a further aspect the invention consists in an assay procedure in which a luminescent labelling compound as defined above is linked with a substance of biological interest, a light emitting reaction is triggered and the amount of the substance is quantified or detected by measuring or sensing the emitted light. The invention is especially applicable to immuno assy, and preferably two-site immunometric assays for the quantitation of polypeptide antigens. Here a solid phase derivative of a polyclonal or monoclonal antibody, which may be an antibody coated tube, microtiter plate well or particulate solid phase, preferably a cellulose derivative, is used to bind antigen molecules. The uptake of antigen, which depends on the antigen concentration, is measured by allowing the resultant solid phase to come into contact with the labelled reagent and measuring the luminescence activity associated with the solid phase following its separation from the assay mixture. Such an assay is preferably performed by adding the solid phase antibody and the "labelled reagent" simultaneously to the antigen containing solution thence allowing the immunological reaction to proceed, preferably for 4 hours, more preferably for 1 hour, before isolation and luminometric measurement of the solid phase. Alternatively the antigen may be reacted first with labelled antibody for a short period of say ½ to 1½ hours and then subsequently with solid phase antibody for a similar period. After isolation of the solid phase, the luminescence activity associated with the solid phase is quantified.

Alternatively indirect determination of the antigen concentration may be performed by using a labelled second antibody which selectively binds the soluble antibody used initially, that is, using unlabelled soluble first antibody. Such a labelled anti (globulin) antibody has the advantage of being a universal labelled reagent.

EXAMPLE

Acridine (10 g) is suspended in water (133 cm$^3$) in which is dissolved potassium cyanide (22 g). Benzoyl chloride (27.5 cm$^3$) is added in a dropwise manner with vigorous shaking of the reaction flask after the addition of each 1 cm$^3$ of benzoyl chloride. The mixture is left to stand for several hours at room temperature, thence filtered and the residual solid washed with distilled water. The solid is then recrystallised from ethanol containing activated decolourising charcoal.

Part of the product of the above procedure, that is, 9-cyano acridine (4 g) is dissolved in sulphuric acid containing 10% by weight of distilled water (total volume equals 40 cm$^3$). The mixture thus obtained is heated at a temperature of 100° C. for 2 hours after which time sodium nitrite (10.7 g) is added slowly with continuous stirring. The resulting mixture is heated at 100° C. for 2 hours then poured into cold, distilled water (650 cm$^3$) The solid material which precipitates at this stage is isolated by filtration and allowed to dissolve in the minimum quantity of one molar sodium hydroxide solution; the solution thus obtained is filtered and the filtrate made slightly acidic by the addition of a 50%, by volume, solution of sulphuric acid in water. The 9-carboxyacridine so formed is then dried in vacuo.

9-carboxyacridine (1.5 g) is added to freshly distilled thionyl chloride (11 cm$^3$) and the mixture heated under reflux for 4 hours. Boiling dichloromethane (100 cm$^3$) is added and the resulting solution filtered. The filtrate is concentrated by distillation and dry heptane added in order to precipitate the 9-chlorocarbonylacridine hydrochloride which is subsequently filtered, washed with dry heptane and dried in vacuo. A portion of the resultant material (0.5 g) is added to dry pyridine (5 cm$^3$) and the mixture stirred for fifteen minutes. Then a molar equivalent of N-succinimidyl 3(4-hydroxyphenyl)-propionate is added. The mixture is stirred at room temperature for twelve hours under anhydrous conditions. The reaction mixture is poured into cold distilled water (100 cm$^3$) acidified to pH2 with hydrochloric acid and the solid material which precipitates collected by filtration and dried in vacuo. Part of the dried material (200 mg) is suspended in freshly distilled dimethyl sulphate (1 cm$^3$) and the mixture heated at 100° C. for ten minutes, the solution formed at this stage is cooled in ice and triturated with dry diethyl ether. The mixture is then filtered and the solid dried in vacuo. The filtrate is retained and evaporated to dryness in vacuo. Both fractions contain chiefly 4-(2-Succinimidyl-oxycarbonylethyl)-phenyl-10-methylacridinium-9-carboxylate methosulphate hereinafter referred to as compound (A).

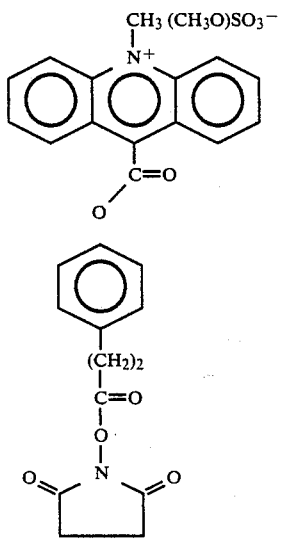

A solution of compound (A) in dry dimethylformamide is made at a concentration of 0.1 mg cm$^{-3}$. Ten microlitres of a 5 mg cm$^{-3}$ solution of monoclonal mouse (anti-human $\alpha_1$ fetoprotein) antibodies are diluted with 300 μl of 0.1 molar phosphate buffer (pH 8.0) containing sodium chloride at a concentration of 0.15 moles per liter. Ten microlitres of the above solution of compound (A) is added to 100 μl of dimethyl formamide and a 10 μl aliquot of this solution removed to a glass test tube. The solution of monoclonal antibodies is then transferred to this tube and the mixture set aside for 15 minutes in the dark at room temperature. One hundred microlitres of a solution of lysine mono-hydrochloride, in the phosphate buffer described above, at a concentration of 10 mg cm$^{-3}$, is then added and the mixture left for a further 15 minutes as described above. The resulting mixture is purified by gel exclusion chromatography using a column of pre-swollen "Sephadex G50", medium grade, of height 250 mm and diameter 10 mm, which has been previously equilibrated with a 0.1 molar phosphate buffer (pH 6.5) containing sodium chloride at a concentration of 0.15 moles per liter, sheep immunoglobulin G at a concentration of 20 mg l$^{-1}$, 0.1% by weight of human serum albumin and 0.01% by weight of thiomersal. The labelled reagent mixture is transferred to the top of the gel column and eluted with the protein-containing buffer whilst collecting 1 cm$^3$ fractions of the column effluent. A 10 μl aliquot of each fraction is measured luminometrically by diluting it to 0.5 cm$^3$ with distilled water and then adding 1 cm$^3$ of a solution of 0.1 moles l$^{-1}$ sodium hydroxide containing 1% by volume of a 100 volume solution of hydrogen peroxide, thence measuring the emitted light by means of a photon counter.

The fraction yielding the greatest emission of light is further purified in a similar manner to that described above and the fraction containing the greatest chemiluminescence emission retained for further use.

The purified "labelled reagent" is used in a two-site inmunochemiluminometric assay in the following manner. A solid phase antibody is prepared by linking an immunoglobulin G fraction of sheep (anti-human $\alpha_1$ fetoprotein) antiserum to a diazonium derivative of reprecipitated aminoaryl cellulose and is stored as a 2 mg cm$^{-3}$ suspension.

This is diluted by a factor of ten such that 100 μl in each assay tube gives 20 μg of solid phase suspended in 0.1 m phosphate buffer (pH 7.4) containing 0.15 moles l$^{-1}$ of sodium chloride and 0.1% by weight of bovine serum albumin.

The "labelled reagent" diluted with the same buffer such that 100 μl in each assay tube yields approximately 30,000 luminescent counts in twenty seconds. A standard solution of human $\alpha_1$-fetoprotein in the same buffer is serially diluted by a factor of two to yield a series of solutions ranging from 400 ng cm$^{-3}$ to 3.2 ng cm$^{-3}$.

Into each of 30 assay tubes is placed 100 μl of the "labelled reagent" solution. One hundred microlitres of the immunoadsorbent suspension is placed into 27 of the same tubes followed by 100 μl of normal male human serum. Into each of 50 assay tubes is placed 100 μl each of the "labelled reagent" solution and immunoadsorbent suspension followed by 100 μl of the diluent buffer. One hundred microlitre aliquots of the standard solutions are added to the human serum containing tubes such that each standard solution was determined in triplicate, three of the first 27 tubes possessed 100 μl of diluent buffer so as to act as a zero $\alpha_1$ fetoprotein standard.

Two 100 μl aliquots are taken from each of 25 serum samples obtained from pregnant women at between 14 and 18 weeks gestational age and added to the remaining 50 assay tubes such that each serum sample is determined in duplicate.

All tubes are incubated for one hour at room temperature after which 2 cm$^3$ of diluent buffer added to each tube except for those three tubes containing "labelled reagent" only. The tubes are centrifuged to sediment the immunoadsorbent, then gently inverted to discard the supernatant. 0.5 cm$^3$ of distilled water is added in turn, with mixing, to each tube which is then placed in the luminometer and the "labelled reagent" determined as described previously.

A dose response curve is constructed for the standards and used to convert the luminescence emission from the serum sample assay tubes to $\alpha_1$ fetoprotein concentration.

Referring to the example above of a synthesis of a N-hydroxysuccinimidyl ester the yield and purity of the final product may be improved by incorporating protection and subsequent deprotection stages in the synthesis. An example of this aspect involves the reaction of the benzylester of 4-hydroxyphenyl propanoic acid with the halocarbonyl acridine followed by removal of the protecting benzyl group and subsequent formation of the N-succinimidyl moiety by esterification of the free acid with N-hydroxysuccinimide.

In the labelling procedure referred to above involving reaction between excess chemiluminescent label and protein, separation of non-protein bound label can also be achieved by prior reaction with other amine containing species such as polylysine or certain solid phase derivatives of amine containing species.

This invention enables the preparation of a chemiluminescent label suitable for use in immuno assay systems which has a sensitivity of detection close to or better than that of the widely used radioisotope label $^{125}$I.

While luminol has been used as a non-isotopic luminescent label for immuno assays it suffers the disadvantages that it is difficult to link to proteins without loss of quantum yield and it requires a catalyst for its oxidative excitation which may generate high background luminescence. The acridinium ester derivative described here is stable, it can be coupled to proteins under mild conditions such that the quantum yield is unaffected and the immunoreactivity of the protein is preserved and it reacts under mild oxidative conditions where background luminescence is minimal.

The assay procedure carried out with acridinium ester labelled antibody is a two-site immunometric assay. Such assays offer advantages over conventional competitive techniques in terms of speed and sensitivity by their use of excess binding reagent as opposed to limiting binding reagent. In the past the advantages of the two-site assay have not been fully realised since incorporation of large amounts of $^{125}I$ to increase specific activity inevitably results in radiolytic damage to antibodies. The chemiluminescent label described in the present invention does not have this disadvantage so that high specific activity labelled antibodies can be prepared without loss of immunoreactivity. The use of acridinium ester labelled antibodies in two-site assays provides a means of improving the sensitivity of measurement of proteins and polypeptides by one to two orders of magnitude by comparison with existing techniques.

What we claim is:

1. A chemiluminescent labelling compound for use in the labelling of substances of biological interest, said compound being capable of undergoing a light emitting reaction and defined by the formula:

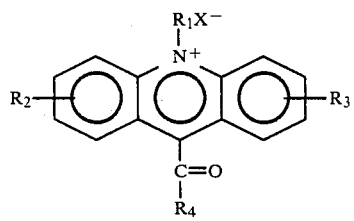

wherein X⁻ is an anion,
 $R_1$ is a substituent selected from the group consisting of hydrogen, alkyl, alkenyl, alkynyl and aryl,
 $R_2$ and $R_3$ are substituents selected from the group consisting of hydrogen, amino, carboxyl, hydroxyl, alkoxyl, nitro and halide, and
 $R_4$ is a substituted phenoxy moiety, with a reactive group capable of reacting with a substance of biological interest being attached, either directly or by means of an alkyl group, to the aryl portion of said phenoxy moiety, said reactive group being selected from the group consisting of:

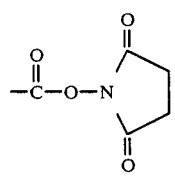 (a)

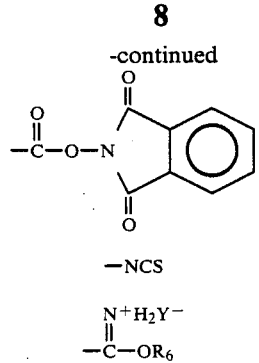

—NCS (c)

$$\underset{\underset{-C-OR_6}{\overset{\|}{O}}}{N^+H_2Y^-}$$ (d)

wherein $R_6$ has the same definition as $R_1$, and Y is a halide,
(e) —halide, and
(f) —azide.

2. A compound according to claim 1, wherein said reactive group is attached to said aryl portion of said phenoxy moiety by means of an alkyl group.

3. A compound according to claim 2, wherein said alkyl group is —CH₂CH₂—.

4. A compound according to claim 1, wherein said reactive group is directly attached to said aryl portion of said phenoxy moiety.

5. A compound according to claim 1, wherein said reactive group is represented by the formula:

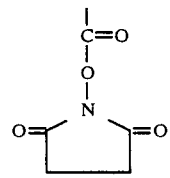

6. A luminescent labelling compound for use in the labelling of substances of biological interest, said compound being of the following formula:

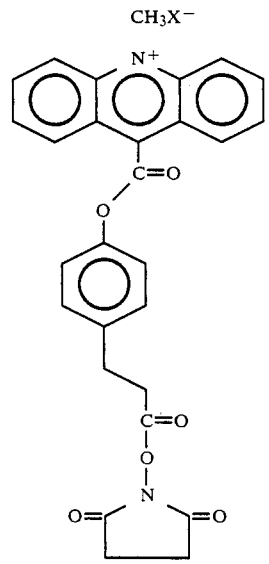

wherein X⁻ is an anion.

7. A compound according to claim 6, wherein X⁻ is (CH₃O)SO₃.

* * * * *